US00PP15776P2

(12) United States Plant Patent
Verwer

(10) Patent No.: US PP15,776 P2
(45) Date of Patent: May 24, 2005

(54) ***DAHLIA* PLANT NAMED 'MELODY LIZZA'**

(50) Latin Name: *Dahlia hybrida*
Varietal Denomination: Melody Lizza

(75) Inventor: Aad W. M. Verwer, Lisse (NL)

(73) Assignee: Verwer-Dahlias BV, Lisse (NL)

( * ) Notice: Subject to any disclaimer, the term of this patent is extended or adjusted under 35 U.S.C. 154(b) by 18 days.

(21) Appl. No.: 10/734,412

(22) Filed: Dec. 12, 2003

(51) Int. Cl.[7] ..... A01H 5/00
(52) U.S. Cl. ..... Plt./321
(58) Field of Search ..... Plt./321

(56) References Cited

PUBLICATIONS

Harris et al. Plant Identification Terminology An Illustrated Glossary. 2001, 2 ed. pp. 61 and 106.*

* cited by examiner

*Primary Examiner*—Anne Marie Grunberg
*Assistant Examiner*—June Hwu
(74) *Attorney, Agent, or Firm*—Wood, Phillips, Katz, Clark & Mortimer

(57) ABSTRACT

A new and distinct *Dahlia* plant named 'Melody Lizza', characterized by its pink-bicolor ray florets, yellow-colored disc florets and vigorous, upright and mounded growth habit.

2 Drawing Sheets

Latin name of genus and species of plant claimed: *Dahlia hybrida.*

Variety denomination: 'Melody Lizza'.

BACKGROUND OF THE INVENTION

The present invention comprises a new and distinct *Dahlia* plant, botanically known as *Dahlia hybrida* and hereinafter referred to by the cultivar name 'Melody Lizza'.

The new cultivar originated as the product of the open pollination of the proprietary breeding selection designated VD-0-9, not patented, during 1997 at Lisse, The Netherlands. The new *Dahlia* was discovered and selected as a single flowering plant within the progeny of the above stated open pollination during the summer of 1998 at Lisse. The Netherlands.

Asexual reproduction of the new cultivar by terminal stem cuttings since 1998 at Lisse, Netherlands and West Chicago, Ill. has demonstrated that the new cultivar reproduces true to type, with all characteristics as herein described, firmly fixed and retained through successive generations of such asexual propagation.

SUMMARY OF THE INVENTION

It was repeatedly found that the cultivar of the present invention:

1. Forms double pink-bicolor ray florets and yellow disk florets.
2. Exhibits a vigorous, upright, and mounded growth habit.

'Melody Lizza' has not been observed under all possible environmental conditions to date. Accordingly, it is possible that the phenotype may vary somewhat with variations in the environment such as temperature, light intensity, and day length without, however, any variance in genotype.

Plants of the new cultivar differ from plants of the female parent primarily in plant height and ray floret color.

Of the many *Dahlia* cultivars known to the inventor, 'Melody Lizza' can be compared to the cultivar 'Melody Dixie' (U.S. Plant Pat. No. 12,911) and the cultivar 'Gallery Bellini' (U.S. Pat. No. 14,162). However, in side by side comparisons, 'Melody Lizza' differs from 'Melody Dixie' in the following characteristics:

1. Plants of 'Melody Lizza' exhibit darker foliage color than do plants of 'Melody Dixie'.
2. The flowers of 'Melody Lizza' are pink-bicolor whereas those of 'Melody Dixie' are cream-white in the center with lilac-purple margins.
3. The plant habit of 'Melody Lizza' is much more branching with shorter internodes than 'Melody Dixie' which has a more stretching habit.

Furthermore, in side by side comparisons 'Melody Lizza' differs from 'Gallery Bellini' in the following characteristics:

1. Plants of 'Melody Lizza' are more branching than plants of 'Gallery Bellini'.
2. Plants of 'Melody Lizza' are taller than plants of 'Gallery Bellini'.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 16 weeks in a greenhouse at West Chicago, Ill.

DETAILED BOTANICAL DESCRIPTION

Figure 1:
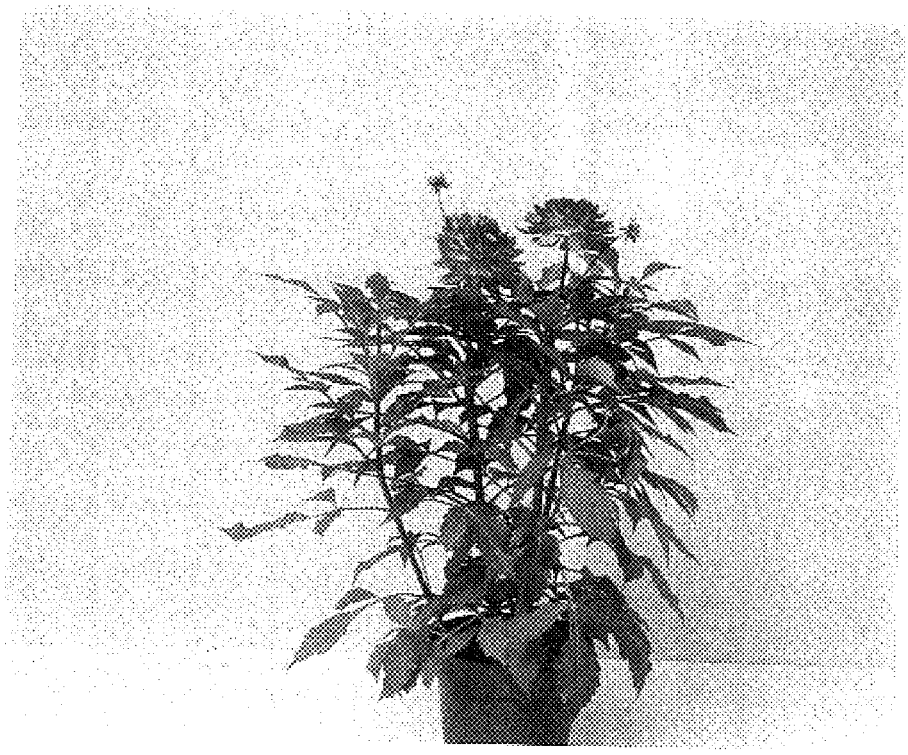
FIG. 1 illustrates a side view of the overall growth and flowering habit of 'Melody Lizza'.
Figure 2:
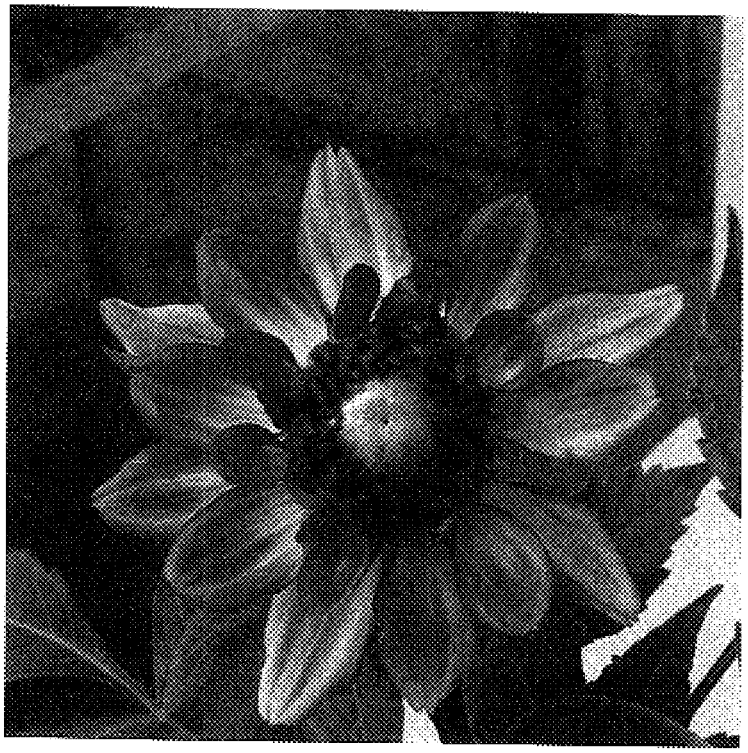
FIG. 2 illustrates a close-up view of a single flower 'Melody Lizza' just opening.
Figure 3:
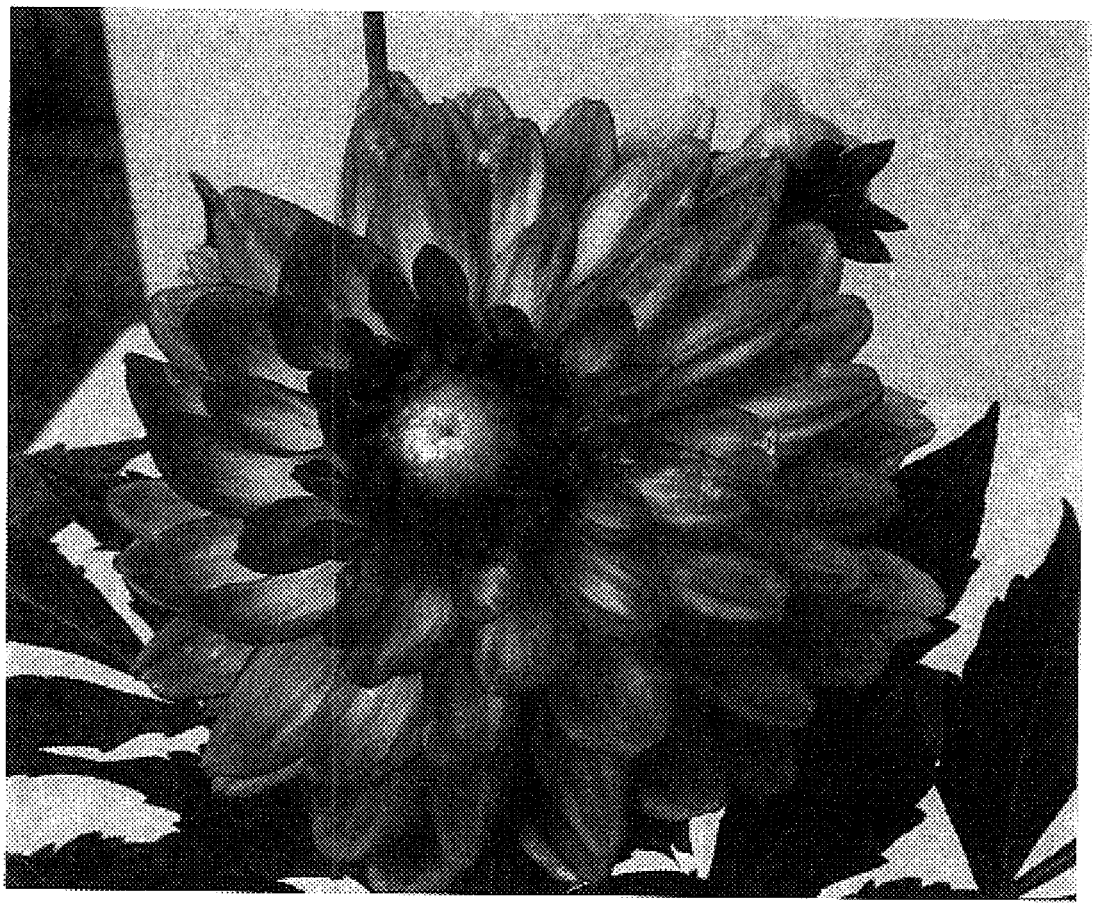
FIG. 3 illustrates a single fully open flower of 'Melody Lizza'.

The chart used in the identification of colors described herein is The R.H.S. Colour Chart of The Royal Horticultural Society, London, England, 1995 edition, except where color terms of ordinary significance are used. The color values were determined on May 21, 2003 in West Chicago, Ill. The readings were taken between 10:00 and 11:45 a.m. under natural light conditions. The plants were produced from cuttings taken from stock plants and were grown in a double polycarbonate-covered greenhouse under conditions comparable to those used in commercial practice. The plants were grown in 15 cm pots for 16 weeks while utilizing a soilless growth medium. Greenhouse temperatures were maintained at approximately 65°–70° F. (18°–21° C.) during the day and approximately 60°–65° F. (15°–18° C.) during the night. Greenhouse light levels were maintained at approximately 4,000–7,000 footcandles during the day. Plants were pinched three weeks after planting of rooted cuttings. The following measurements and descriptions were taken at 16 weeks after planting of rooted cuttings.

Botanical classification: *Dahlia hybrida* cultivar 'Melody Lizza'.

Parentage: Open pollination of the proprietary *Dahlia* breeding selection designated VD-0-9.

Propagation:

*Type cutting.*—Terminal tip.

*Time to initiate roots.*—Approximately 7 to 10 days.

*Time to develop roots.*—Approximately 21 to 28 days.

*Rooting habit.*—Freely branching.

*Root description.*—Fine, fibrous.

*Tubers.*—Will form under short day conditions of at least 13 to 14 hours of darkness.

Plant description:

*General appearance and habit.*—Upright, mounded and vigorous.

*Crop time.*—Approximately 65–70 days to first flower.

*Size.*—Height from top of soil to top of plant plane: Approximately 49.3 cm. Width: Approximately 44.2 cm.

*Branching habit.*—Basal branching, pinching enhances branching.

*Branch description.*—Strength: Strong. Quantity per plant: Approximately 4. Length: Approximately 30.8 cm. Diameter: Approximately 7.7 mm. Color: 143B with overlay of 183A. Texture: Glabrous. Length of $4^{th}$ internode: Approximately 6.1 cm.

*Foliage.*—Form: Both simple and compound. Quantity of leaves per lateral branch: Approximately 18. Quantity of leaflets per leaf: 3 or 5. Leaf/leaflet: Shape: Ovate. Margin: Serrate. Apex: Acuminate. Base: Attenuate. Arrangement: Opposite. Venation pattern: Pinnate. Texture: Upper surface: Hispidulous, slightly rugose. Size of simple leaves: Length: Approximately 8 cm. Width: Approximately: 3 cm. Petiole length: Approximately 4 cm. Diameter: Approximately 3 mm. Size of mature trifolate leaves: Length: Approximately 12.4 cm. Width: Approximately 11.2 cm. Petiole of compound leaf: Length: 5.2 cm. Diameter: 4 mm. Color: 144A with overlay of 184A. Size of terminal leaflets: Length: Approximately 8.4 cm. Width: Approximately 4.4 cm. Size of lateral leaflets: Length: Approximately 6.4 cm. Width: Approximately 2.9 cm. Color of young foliage: Upper surface: 137A with venation of 146C. Lower surface: 191A with venation of 146B. Color of mature foliage: Upper surface: Darker than 147A with veins of 147B. Lower surface: Closest to 191A with veins of 146B.

Inflorescence description:

*Outdoor flowering habit.*—'Melody Lizza' is freely flowering under outdoor growing conditions was substantially continuous blooming from spring through fall.

*Appearance.*—Fully double, arising from leaf axils on strong peduncles, positioned just over the foliage. Quantity per plant: Approximately 3 inflorescences open at any one time. Disc and ray florets arranged acropetally on a capitulum. Persistent.

*Lastingness of bloom.*—Approximately 4 weeks from first open ray floret to senescence.

*Flower bud.*—Rate of opening: Approximately 2 weeks from first color to full bloom. Shape: Oblate. Bud just before color: Length: Approximately 1.8 cm. Width: Approximately 1.3 cm. Color: 151A. Bud at first color: Length: Approximately 2.1 cm. Diameter at first color: Approximately 1.7 cm. Color: N74A.

*Shape/size.*—Hemispherical. Diameter: Approximately 11.7 cm. Depth: Approximately 7 cm. Disc diameter: Approximately 1.3 cm. Receptacle diameter: Approximately 2 cm. Receptacle height/depth: Approximately 5 mm. Receptable texture: Rough.

*Fragrance.*—None.

*Ray florets.*—Quantity: Approximately 311 per inflorescence arranged in approximately 11 whorls. Shape: Elongated, cupped. Length: Approximately 5 cm. Width: Approximately 1.7 cm. Apex: Obtuse to emarginate with two or three tips. Base: Fused to form tube. Margin: Entire. Texture: Glabrous. Color: Fully opened, upper surface: Mixture of longitudinal areas of alternating and blending of 73C and 67C with venation of 155D, margin of 67A and base of N155B. Fully opened, lower surface: 73C with venation of 155D, margin of 67A and base of N155B.

*Disc florets.*—Disc florets develop after most of the ray florets have died. Quantity: Approximately 30. Shape: Elongated, cylindrical. Texture: Glabrous. Color: Transparent, 9A at apex, 150D at base.

*Peduncle.*—Strong, erect. Length: Approximately 12 cm. Diameter: Approximately 3 mm. Texture: Glabrous. Color: 144B.

*Outer involucral bracts.*—Quantity: Approximately 8. Shape: Lanceolate. Tip: Acute. Margin: Entire. Texture: Glabrous. Color of upper and lower surfaces: 146A with parallel venation of 150A.

*Inner involucral bracts.*—Quantity: One per floret. Shape: Lanceolate. Margin: Entire. Apex: Acute. Length: 1.3 cm. Width: 4 mm. Color: Transparent, 150C at apex, 150D at base.

*Reproductive organs.*—Androecium — On disc florets. Stamen number: 4. Anther length: Approximately 3.5 mm. Anther color: 9A. Pollen amount: Abundant. Pollen color is 21A. Gynoecium — On disc and ray florets. Pistil length: Approximately 1.3 cm. Stigma length: 4 mm. Stigma color: 9A. Style length: 6 mm. Style color: 150D. Ovary length: 2 mm. Ovary color: 145B.

Seed and fruit production: Neither seed nor fruit production has been observed.

Disease and pest resistance: Resistance to pathogens and pests common to *Dahlia* has not been observed.

Hardiness zone: 'Melody Lizza' is presumably hardy in zones nine (9) and above.

It is claimed:

1. A new and distinct cultivar of *Dahlia* plant named 'Melody Lizza' substantially, as herein shown and described, which:

1. Forms double, pink bi-colored ray florets and yellow-colored disc florets.
2. Exhibits a vigorous, upright, and mounded growth habit.

* * * * *